(12) United States Patent
Dinkler, II

(10) Patent No.: US 8,939,976 B2
(45) Date of Patent: Jan. 27, 2015

(54) LIMITED ARTIFACT SKULL PIN

(76) Inventor: Charles E. Dinkler, II, Dayton, OH (US)

( * ) Notice: Subject to any disclaimer, the term of this patent is extended or adjusted under 35 U.S.C. 154(b) by 1965 days.

(21) Appl. No.: 12/100,687

(22) Filed: Apr. 10, 2008

(65) Prior Publication Data

US 2008/0251086 A1    Oct. 16, 2008

Related U.S. Application Data

(60) Provisional application No. 60/911,713, filed on Apr. 13, 2007.

(51) Int. Cl.
*A61F 17/00*    (2006.01)

(52) U.S. Cl.
USPC .................................. 606/53; 606/54; 606/59

(58) Field of Classification Search
USPC .............. 606/54–59, 130; 600/424–429, 207, 600/411, 417; 378/204–205; 602/32, 36, 602/39; 128/869, 845–846
See application file for complete search history.

(56) References Cited

U.S. PATENT DOCUMENTS

| | | | |
|---|---|---|---|
| 5,197,965 A * | 3/1993 | Cherry et al. | 606/54 |
| 5,302,170 A * | 4/1994 | Tweardy | 602/17 |
| 5,643,268 A * | 7/1997 | Vilsmeier et al. | 606/308 |
| 6,896,678 B2 * | 5/2005 | Tweardy | 606/916 |
| 7,011,619 B1 * | 3/2006 | Lewis et al. | 600/3 |
| 7,246,975 B2 * | 7/2007 | Corso et al. | 408/206 |
| 7,905,884 B2 * | 3/2011 | Simonton et al. | 606/79 |
| 8,104,477 B2 * | 1/2012 | Edlauer et al. | 128/845 |
| 2007/0270801 A1 * | 11/2007 | Arn et al. | 606/54 |

\* cited by examiner

*Primary Examiner* — Michael A. Brown
(74) *Attorney, Agent, or Firm* — Hasse & Nesbitt LLC; Daniel F. Nesbitt

(57) ABSTRACT

A skull pin assembly for a head fixation device that allows for effective imaging with limited artifact is disclosed. The skull pin assembly comprises two components, a tip and a housing. The conical-shaped tip component engages the skull at a point and is configured to fit within the bore of the substantially cylindrical non-conductive housing component. The conical skull pin tip can be comprised of a material that causes limited artifact in medical imaging procedures. The conical skull pin tip can taper away from the point engaging the skull at a first angle and can seamlessly transition into a conical-shaped surface of the housing component. In one embodiment, a third surface of the housing component can also be tapered to meet the first surface of the tip component at the identical first angle of tapering.

19 Claims, 5 Drawing Sheets

LIMITED ARTIFACT SKULL PIN

CROSS-REFERENCE TO RELATED APPLICATIONS

This application claims the benefit of U.S. Provisional Application Ser. No. 60/911,713 (DIN 0001 MA), filed Apr. 13, 2007.

BACKGROUND OF THE INVENTION

The present invention generally relates to a skull pin assembly used with surgical head frames and, in particular, relates to a seamless tip and housing skull pin assembly used in surgical head fixation devices, such as skull clamps, which allows for effective imaging of a patient's skull while undergoing imaging procedures, such as computed tomography (CT) and magnetic resonance imaging (MRI).

Skull pins typically are used in surgical head fixation devices for rigidly supporting the head of a patient during neurosurgical and cervical spine procedures. A typical head fixation device is illustrated in FIG. 1. The head fixation device 100 works like a clamp, or vise, to keep the head of the patient steady as surgeries are performed. Typically, on one side of the head fixation device is a rocker arm 110 containing two skull pins 115 and on the opposing side is a mechanism 120 to engage and advance a third pin 125 into the skull of the patient. When the skin on the skull of the patient is engaged with the skull pins, it is important that the skull pin pierces the skin and does not disrupt its movement as the skull pin further engages the skull bone. Certain skull pin designs for children have been known to cause necrosis where the area just behind the tip of the skull pin compresses the skin of the skull. Therefore, it is desirable to have the tip and housing surfaces of the skull pin assembly create a continuous transition where the tip and housing meet.

After the skull pins are positioned onto the patient's skull, a potential problem may occur when a diagnostic scan of the head is needed after the placement of the head fixation device. The problem may occur when the skull pins are in the area needing scanned. Since the head fixation device and skull pins are optimally located on the head for fixation and support, the skull pins may be in a less desirable location with regard to the imaging plane. Additionally, the skull pins are typically comprised of a metal or some other conductive material that may cause artifact to appear on the images. An artifact is any visible feature or distortion in an output image that is not present in the object being scanned. Artifacts generally degrade an image, and, if severe enough, can impair interpretation of the image. The problem of skull pins causing artifact is becoming more common due to surgical imaging procedures being performed intra-operatively (i.e., a magnetic resonance (MR) or a computed tomography (CT) scanning machine is employed in the operating room). Surgeons frequently want to treat the patient by using such an imaging machine to scan the head of a patient during the surgical procedure; however, the metallic, or conductive, skull pins in the head fixation device stabilizing the patient's head may cause artifact on the scanned images.

Therefore, there is a need for skull pins that rigidly supports the head of a patient in a head fixation device during neurosurgical and related procedures which allows for effective imaging of the head of the patient with the skull pin in place.

There is yet another need for a skull pin assembly comprised of two components, a tip and a housing, where the meeting surfaces of the two components creates a continuous and seamless transition from tip to housing where the components meet, in order to prevent the disruption of the movement of the skin on the head as the pin pierces the skin and further engages the skull bone.

There is still another need for a cost effective skull pin assembly where the skull pin assembly provides limited artifact in a variety of different imaging situations while providing easy of use.

BRIEF SUMMARY OF THE INVENTION

According to the present invention, a skull pin assembly for a head fixation device that allows for effective imaging with limited artifact is disclosed. The skull pin assembly comprises two components, a tip and a housing. The conical-shaped tip component engages the skull at a point and is configured to fit within the bore of the substantially cylindrical non-conductive housing component. The conical skull pin tip can be comprised of a material that causes limited artifact in medical imaging procedures. The conical skull pin tip can taper away from the point engaging the skull at a first angle and can seamlessly transition into a conical-shaped surface of the housing component. In one embodiment, the housing component can also be tapered to meet the tip component at the identical first angle of the first surface of the tip component.

Accordingly, it is a feature of the embodiments of the present invention to produce a skull pin assembly for a head fixation device that can stabilize and rigidly support the head of the patient and that can allow for effective imaging with limited artifact.

It is another feature of the embodiments of the present invention to produce a skull pin assembly for a head fixation device where the skull pin tip can seamlessly transition into the skull pin housing.

It is yet another feature of the embodiments of the present invention to produce a head fixation skull pin assembly that is cost effective for a variety of imaging situations. Other features of the embodiments of the present invention will be apparent in light of the description of the invention embodied herein.

BRIEF DESCRIPTION OF THE SEVERAL VIEWS OF THE DRAWINGS

The following detailed description of specific embodiments of the present invention can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the invention may be practiced. It is to be understood that other embodiments may be utilized and that logical, mechanical and electrical changes may be made without departing from the spirit and scope of the present invention.

Figure 1:
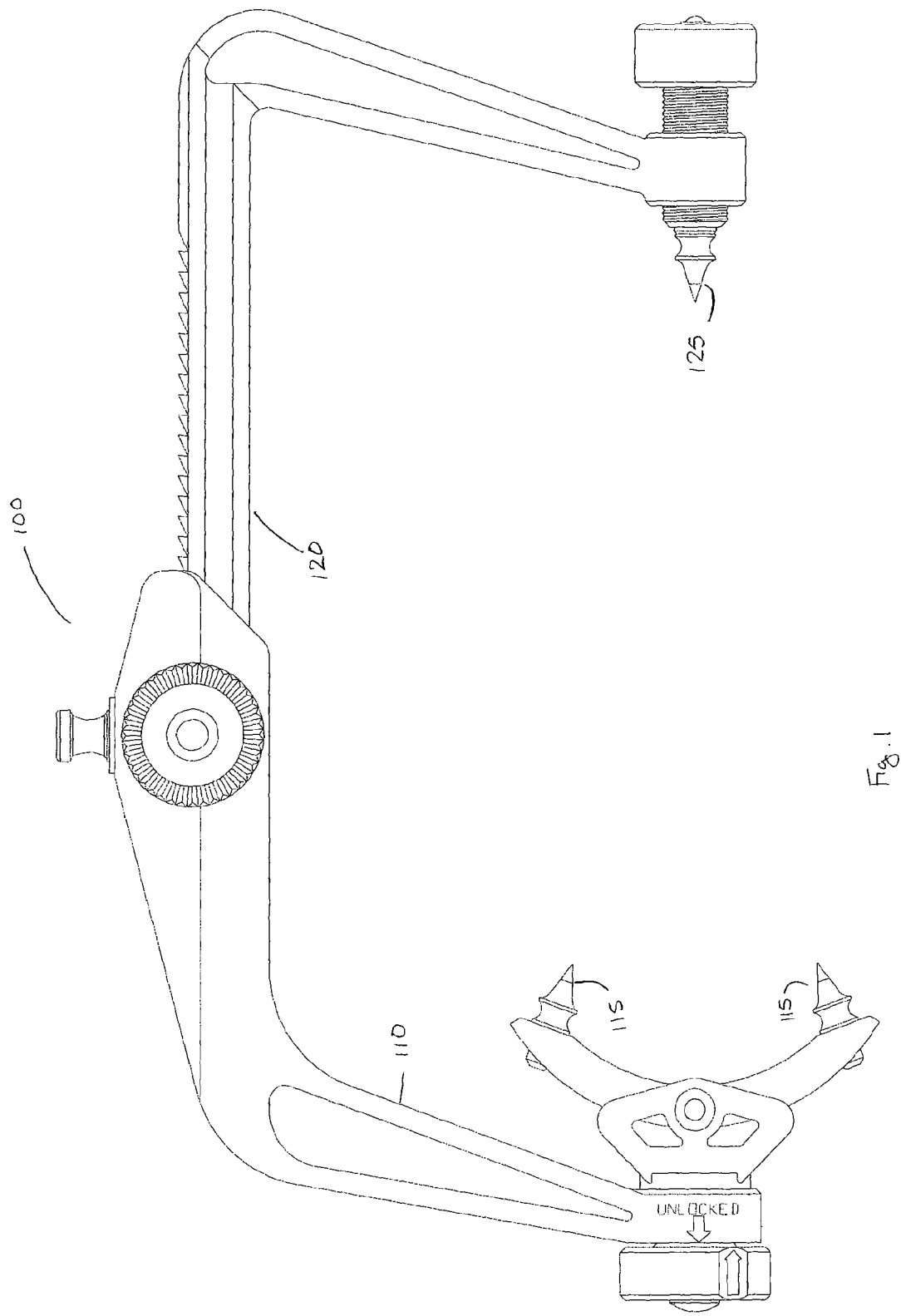
FIG. 1 illustrates a typical head fixation device.
Figure 2:
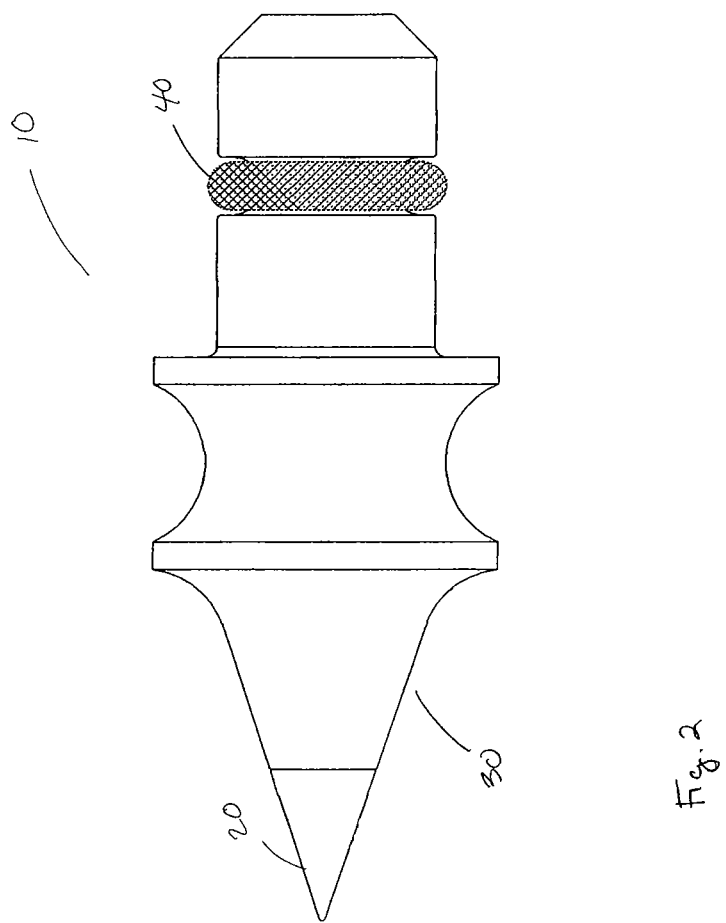
FIG. 2 illustrates a skull pin assembly according to an embodiment of the present invention.

Referring initially to FIG. 2, a skull pin assembly 10 according to one embodiment of the present invention is illustrated. The skull pin assembly 10 can be used in a head fixation device such as, for example, a skull clamp, that can be used to keep the head of a patient rigidly supported during neurosurgical and other related procedures requiring the immobilization of the head. The skull pin assembly 10 can be comprised of at least two components, a skull pin tip 20 and a skull pin housing 30. The first component, the skull pin tip 20, can be uniquely designed to use the least amount of material capable of rigidly holding the head but, at the same time, not producing image artifact during imaging scans.

Image artifact can be thought of as something artificial, a distortion that does not reflect normal anatomy or pathology, that is not usually found in the body. For example, in radiology, the appearance on an X-ray of a surgical metal clip that obscures the clear view of an anatomical structure. Artifacts from metal frequently appear as regions of empty space around the metal object—frequently called "black-hole artifact." CT artifacts from metals can be seen, for example, as dark lines or streaks through the scan, which radiate from the object making the features in the scan indiscernible. Additionally, distortion, in a MRI scan, can be the result of using magnetic materials that "bend" the features or can give the impression that the feature is where it is not. Therefore, a limited artifact skull pin can be a skull pin that projects no, or very few, lines or streaks that can make the features of the scan difficult to interpret and/or that causes no, or very little, magnetic interference, distortion, of the scanned features. The least amount of material can be desired so that materials known to produce undesirable imaging characteristics can still be used. Additionally, using ferromagnetic materials and excessive amounts of titanium can cause thermal injury from radio-frequency induction heating of the object.

The second component, the skull pin housing 30, can house the skull pin tip so that it can be secured to a head fixation device. The skull pin housing 30 can comprise a material that does not produce image artifact. In one embodiment, the skull pin assembly 10 can further comprise an O-ring 40. The O-ring 40 can help ensure a tight and secure fit of the skull pin assemblies 10 into the head fixation device so that the skull pin assembly 20 does not unintentionally separate from the head fixation device.

Figure 3:
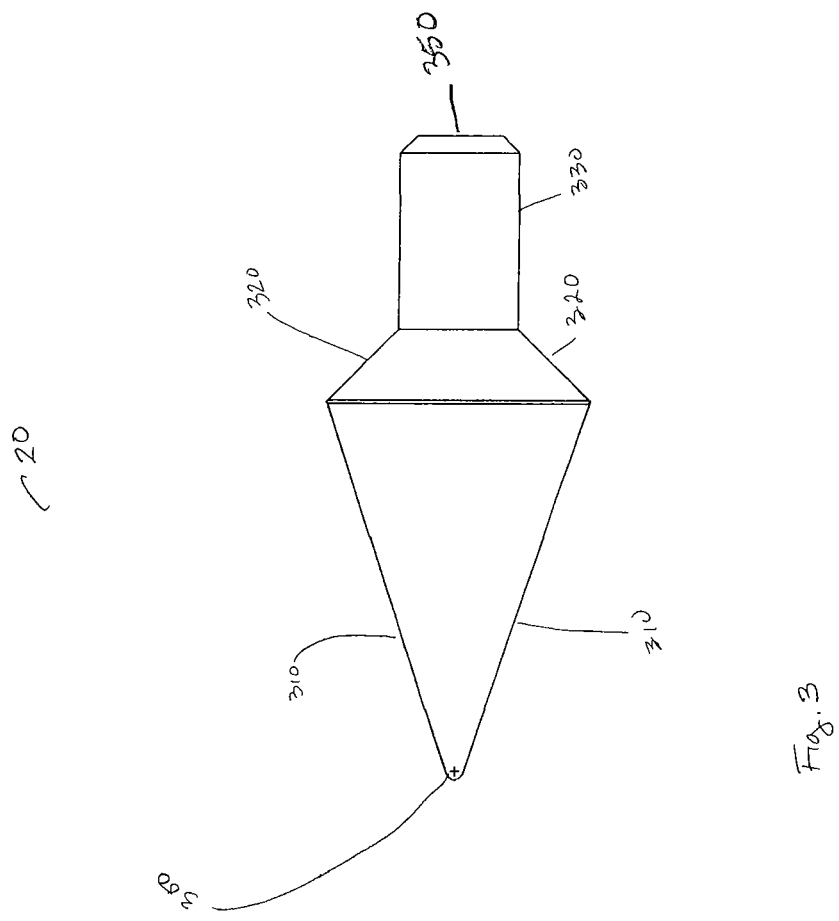
FIG. 3 illustrates the pin tip of the skull pin assembly of FIG. 2 according to an embodiment of the present invention.

Referring to FIG. 3, the skull pin tip 20 component is illustrated. The pin tip component 20 can have a conical point 300 at one end for engaging the skull of the patient. In one embodiment, the conical point 300 can have a radius of curvature between about 0.005 inches to about 0.010 inches. The other end 350 of the skull pin component 20 can be adapted to fit into the bore 410 at one end 415 of the housing component 30, see FIG. 4. The skull pin tip component 20 can engage the outer skull bone of the patient and can be used to drive the skull pin assembly 10 into the skull bone until the skull pin assembly 10 is seated at a desired force. For a typical adult patient, the desired force can be between about 60 to about 80 pounds of force. For children, five years or older, the desired force can be less than about 60 pounds. Skull pin assemblies 10 typically are not used for children under the age of five. The amount of force can be dependent on the patient and the surgeon.

Figure 4:
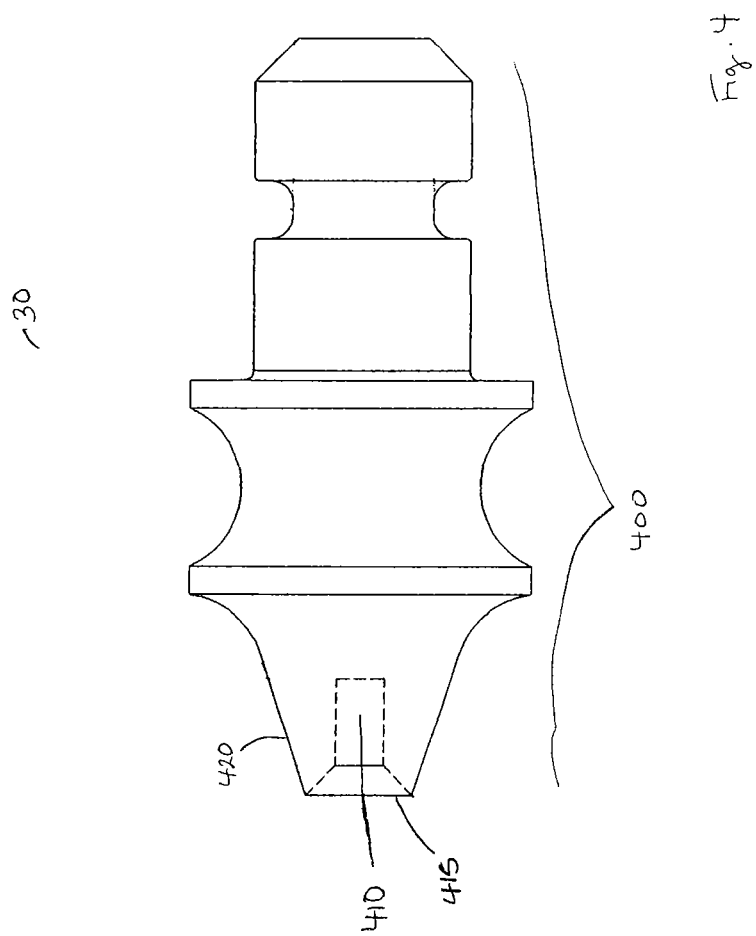
FIG. 4 illustrates the housing of the skull pin assembly of FIG. 2 according to an embodiment of the present invention.

The first surface 310 of the conical point 300 of the skull pin tip component 20 can taper away from the end of the point 300 engaging the skull at a first angle and can transition into an identical sloping third surface 420 of the housing component 30 (see FIG. 4). In one embodiment, the first surface 310 can taper away from the end of the conical point 300 at an included angle of approximately 37 degrees with respect to the central axis of the skull pin tip component 20. The first surface 310 can terminate in a short second conical surface 320 tapered in substantially the opposite direction from the first surface 310. In one embodiment, the second conical surface 320 can taper at an included angle of approximately 45 degrees with respect to the tip central axis. The second conical surface 320 can terminate in a short substantially cylindrical section of elongation 330 for engaging the housing 30. The second conical surface 320 and the elongation section 330 form a 135 degrees. In one embodiment, the skull pin tip component 20 can have an overall length that can range from about 0.385 inches to about 0.375 inches and an overall width that can range from about 0.156 inches to about 0.152 inches. The first surface 310 can have a length that can range from about 0.225 inches to about 0.215 inches. The second surface 320 can have a length that can range from about 0.045 inches to about 0.040 inches. Finally, the elongation section 330 can have a length that can range from about 0.130 inches to about 0.120 inches and a diameter that can range from about 0.085 inches to about 0.065 inches.

The skull pin tip component 20 can have the necessary material properties to be driven with enough force into the skull of the patient and the strength to hold the weight of the patient's head during the surgical procedure while producing limited artifact in any imaging produces performed while the skull pin assembly is seated in the skull. Typically, a patient's head weighs approximately ten pounds. In one embodiment, the skull pin tip component 20 may be comprised of titanium. Titanium is non-magnetic and, therefore, can be useful as a skull pin tip component 20 when the surgeon needs to perform MR imaging in the operating room. However, the volume of titanium material used in the skull pin tip component 20 should be closely monitored. If too much titanium is used, the titanium skull pin tip component 20 can produce too much heat and could potentially burn the patient at the location where the skull pin tip component 20 is placed in the skull of the patient. Additionally, the grade of titanium used should be considered. The material properties of commercially pure titanium are not desirable because they do not adequately penetrate the skull bone. However, titanium alloys can have the desired material properties. A titanium skull pin tip component 20 may also work during CT imaging. However, the size of the skull pin tip component 20 should be taken into account during CT imaging. For example, if the skull pin tip component 20 is metallic, or conductive, and too large, the tip component 20 may produce unacceptable artifact in CT images. For example, unacceptable artifact would result in the projection of a beam of rays across the scan making the features indiscernible.

In another embodiment, the skull pin tip component 20 may be comprised of stainless steel. Stainless steel can be relatively cheap but tends to produce artifact in both MR and CT images. However, a surgeon can use the head fixation device with a stainless steel skull tip component 20 when using an X-ray machine in the operating room. A stainless steel skull pin tip component 20 can work well with an X-ray machine since only a "slice" of the head of the patient may be being imaged at any given time. Therefore, a stainless steel skull pin tip component 20 may work well in head fixation devices when CT or MR imaging is not required.

In still another embodiment, the skull pin tip component 20 may be comprised of a ceramic. Ceramic is non-magnetic and non-conductive. However, a ceramic skull pin tip component 20 can work well in MR imaging but may not work as well for CT imaging. Ceramic skull pin tip components 20 can have very high strength with little elongation resulting in brittleness.

In yet another embodiment the skull pin tip component 20 may be comprised of sapphire. Sapphire is also non-magnetic and non-conductive. Sapphire skull pin tip components 20 can perform well in both CT and MR imaging. Sapphire can have very high strength with little elongation. However, sapphire can be brittle and can be costly to manufacture.

In still yet another embodiment, the skull pin tip component 20 may be comprised of beryllium. Beryllium is non-magnetic and can work well in CT and MR imaging. However, a beryllium skull pin tip component 20 can require an additional coating on the surface of the beryllium skull pin tip component 20 due to carcinogenic properties of beryllium.

Turning now to FIG. 4, the skull pin housing component 30 is illustrated. The skull pin housing component 30 can comprise a substantially cylindrical non-conductive body 400. The skull pin housing component 30 can have an opening 410, or bore, at a first end 415 of the cylindrical body 400 that can be adapted to receive the second conical surface 320 and the elongated cylindrical section 330 of the skull pin tip 20. Frictional force between the elongated cylindrical section 330 and cylindrical non-conductive body 400 can keep the skull pin component 20 and the housing component 30 together. A third conical surface 420 can taper away from the first end 415 of the skull pin housing component 30 at an angle that can be identical to the slope of the first surface 310 of the skull pin tip component 20. In one embodiment, the third conical surface 420 can taper away from the first end 415 at an included angle of approximately 37 degrees with respect to the central axis such that the first surface 310 of the skull pin tip component 20 can seamlessly transition into the third conical surface 420 of the skull pin housing component 30.

In one embodiment, the overall length of the housing component 30 can be about 1.33 inches. Additionally, the end 420 can have a length of about 0.290 inches and a diameter that ranges from about 0.152 inches where the housing component 30 can be configured to receive the tip component 20 to about 0.50 inches. The length of the tip component 20 and the end 420 of the housing component can be about 0.520 inches. Having the first surface 310 of the skull pin tip component 20 and the third surface 420 of the skull pin housing component 30 sloped at the same angle can create a continuous transition where the two components 20, 30 come together. Having a seamless continuous transition between the two components 20, 30, the skull pin assembly 10 may not disrupt the movement of the skin as the skull pin tip component 20 pierces the skin and further engages the skull bone.

The skull pin housing component 30 material should be different from the pin tip component 20 material in order to allow the skull pin assembly 10 to avoid artifact and to be effective in imaging procedures as well as making the skull pin assembly 10 cost effective. The skull pin housing component 30 can be comprised of a non-conductive material such as, for example, a polymer resin. The polymer resin can be, for example, a thermoplastic such as, for example, polyetheretherketones (PEEK) but, any other suitable non-conductive material may be used. Fillers, such as carbon or any other suitable filler, may be added to the polymer resin to promote strength of the skull pin housing component 30. In one embodiment, the filler can be 10% carbon.

Figure 5:
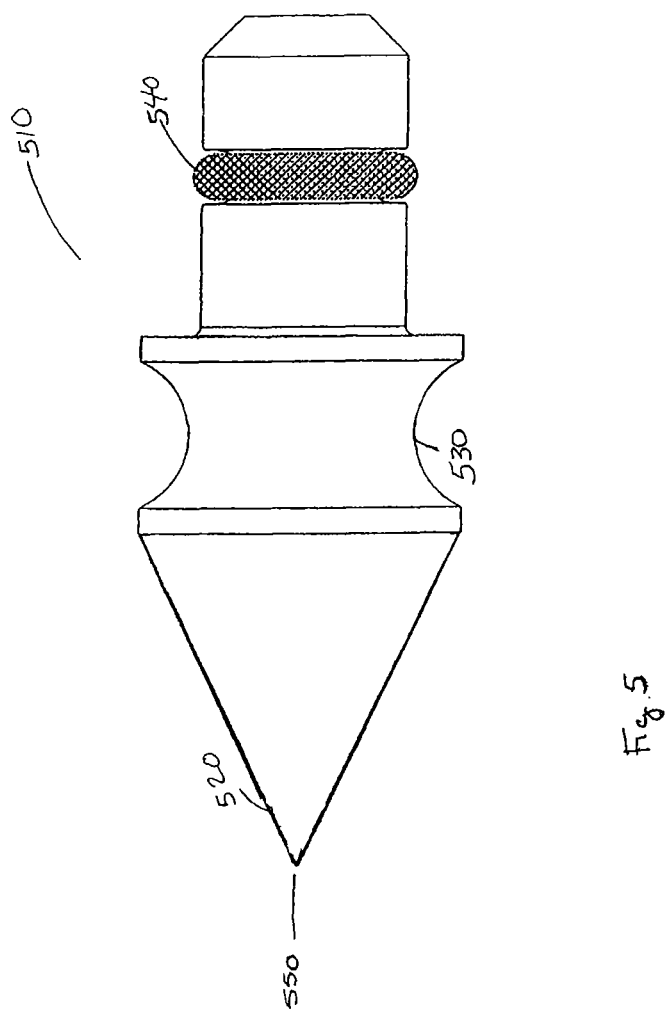
FIG. 5 illustrates another skull pin assembly according to an embodiment of the present invention.

Another embodiment of the skull pin assembly 510 is illustrated in FIG. 5. In this embodiment, the skull pin assembly 510 can be comprised of two components, a skull pin tip component 520 and a skull pin housing component 530. In one embodiment, the skull pin assembly 510 can also comprise an O-ring 540 which can be utilized as described above. In this embodiment, the skull pin tip component 520 can be tapered away from its conical end point 550 at a first angle until it reaches the full diameter of the substantially cylindrical body of the skull pin housing component 530. In other words, the end of the housing skull pin housing component 530 that can be adapted to receive the skull pin tip component 520 is not sloped to meet the skull pin tip component 520. The skull pin tip component 520 can engage the skull pin housing component 520 in a manner similar to the method described above for the other embodiment. In one embodiment, the full diameter of the cylindrical body of the housing component can be about 0.50 inches and the overall length of the skull pin tip component can be about 0.520 inches.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:
1. A skull pin assembly, the assembly comprising:
a tip component for engaging a skull of a patient, the tip component comprising
a conical point to be positioned against the skull,
a first conical surface that tapers away from the conical point at a first angle,
a second conical surface that tapers in an opposite direction from the first surface at a second angle, and
a substantially cylindrical elongation section connected to the second conical surface,
wherein the tip component is comprised of a material that produces limited artifact during image scanning; and
a substantially cylindrical non-conductive housing component comprising,
a first end, wherein the first end has an opening configured to engage the second surface and the cylindrical elongation section of the tip component into the housing component,
a third conical surface tapering from the first end at the first angle such that the transition from the first conical surface of the tip component to the third conical surface of the housing component is seamless, and
a second end configured to securely engage with a head fixation device.

2. The assembly of claim 1, further comprising, an O-ring positioned about the second end of the non-conductive housing for securing the skull pin assembly to the head fixation assembly.

3. The assembly of claim 1, wherein the second angle is about 45 degrees with respect to the central axis of the tip component.

4. The assembly of claim 1, wherein the housing component is comprised of a polymer resin.

5. The assembly of claim 4, wherein the polymer resin comprises additional fillers for strength.

6. The assembly of claim 5, wherein the fillers are comprised of carbon.

7. The assembly of claim 4, wherein the polymer resin is a thermoplastic.

8. The assembly of claim 7, wherein the thermoplastic is polyetheretherketone.

9. The assembly of claim 1, wherein the first angle is about 37 degrees with respect to the central axis of the tip component.

10. The assembly of claim 1, wherein the tip component is selected from the group consisting of titanium, a titanium alloy, stainless steel, ceramic, sapphire, beryllium, and combinations thereof.

11. The assembly of claim 10, wherein the tip component comprises a titanium alloy for use in magnetic resonance image scanning, computed tomography scanning or combinations thereof.

12. The assembly of claim 10, wherein the tip component comprises stainless steel for use with X-ray imaging.

13. The assembly of claim 10, wherein the tip component comprises ceramic for use with magnetic resonance image scanning.

14. The assembly of claim 10, wherein the tip component comprises sapphire for use in magnetic resonance image scanning, computed tomography scanning or combinations thereof.

15. The assembly of claim 10, wherein the tip component comprises beryllium for use with computed tomography scanning, magnetic resonance image scanning or combinations thereof.

16. The assembly of claim 15, wherein a beryllium tip component comprises a surface coating.

17. The assembly of claim 1, wherein the substantially cylindrical elongation section is connected to the second conical surface at a third angle.

18. The assembly of claim 1, wherein the tip component further includes a second conical surface that tapers in an opposite direction from the first surface at a second angle.

19. The assembly of claim 1, wherein to opening in the first end of the housing opens to a bore, the bore having an inner conical surface extending inwardly from the opening to engage the second surface of the tip component, and a cylindrical surface extending from the inner conical surface to engage the cylindrical elongation section of the tip component.

* * * * *